United States Patent [19]

Sato et al.

[11] Patent Number: 5,127,271
[45] Date of Patent: Jul. 7, 1992

[54] METHOD OF NON-DESTRUCTIVE INSPECTION FOR RESINOUS AUTOMOTIVE BUMPER BEAMS

[75] Inventors: Shoji Sato; Yoji Ushiki; Hisashi Masuda, all of Sayama, Japan

[73] Assignee: Honda Giken Kogyo Kabushiki Kaisha, Tokyo, Japan

[21] Appl. No.: 634,570

[22] Filed: Dec. 27, 1990

[30] Foreign Application Priority Data

Dec. 27, 1989 [JP] Japan .................. 1-339785

[51] Int. Cl.$^5$ ............................................. G01N 3/20
[52] U.S. Cl. ........................................................ 73/852
[58] Field of Search .......................... 73/852, 853, 849

[56] References Cited

U.S. PATENT DOCUMENTS

| | | | |
|---|---|---|---|
| 2,032,989 | 11/1931 | Kenney et al. | 73/852 |
| 4,213,349 | 7/1980 | Miura | 73/852 |
| 4,313,348 | 2/1982 | Madsen | 73/852 |
| 4,573,360 | 3/1986 | Yoneda | 73/852 |
| 4,589,288 | 5/1986 | Porter et al. | 73/852 |

FOREIGN PATENT DOCUMENTS

| | | |
|---|---|---|
| 0232573 | 8/1987 | European Pat. Off. |
| 63-89311 | 4/1988 | Japan . |
| 63-91224 | 4/1988 | Japan . |
| 1018726 | 2/1966 | United Kingdom . |
| 2043265 | 10/1980 | United Kingdom . |
| 2148517 | 5/1985 | United Kingdom . |

Primary Examiner—Hezron E. Williams
Assistant Examiner—Howard Wisnia

[57] ABSTRACT

A method of non-destructive inspection for resinous automotive bumper beams provides for applying a flexural load to the center of a bumper beam by a pressing jig in a state where both ends of the bumper beam have been pivotably supported to gradually bend the bumper beam, measuring or determining the bending strain and energy absorption of the bumper beam upon the application of the flexural load, said energy absorption being calculated from said bending strain and flexural load, and judging the bumper beam to be good in quality only when the energy absorption of the bumper beam reaches at least a control value of the energy absorption, which is set up in advance, in a state that the bending strain of the bumper beam is at most a control value of the bending strain, which is set up in advance. The control value of the energy absorption is determined by correcting the value of energy absorption upon destruction of a bumper beam, which has been found in a standard destructive test. The control value of the bending strain is determined by correcting the bending strain in the standard destructive test. These corrections are performed on the basis of the correlations between a plurality of data as to the energy absorption and bending strain in the standard destructive test and a trial destructive test, respectively.

3 Claims, 6 Drawing Sheets

METHOD OF NON-DESTRUCTIVE INSPECTION FOR RESINOUS AUTOMOTIVE BUMPER BEAMS

BACKGROUND OF THE INVENTION (1) Field of the Invention

The present invention relates to a method of non-destructive inspection for resinous automotive bumper beams.

(2) Description of the Related Art

Recently, resinous automotive bumper beams, which have been obtained by heating and softening a plurality of elongate stampable sheets formed of a long-fiber-reinforced composite thermoplastic material containing, for example, longitudinally-stretching fibers as a reinforcement to laminate them and then press-molding the resulting laminate, have begun to be used in place of conventional metallic automotive bumper beams with a view toward reducing their weight and improving their capability of absorbing shock.

The bumper beams for automobiles are first of all required to have a function capable of reducing shock in a collision or the like and to absorb striking energy to at least a predetermined standard value upon a collision. In this case, since the bumper beams absorb the striking energy by their bending, they are secondarily required not to bend to such an extent that they strike on the automotive bodies before they absorb the energy to the predetermined standard value, namely, to have flexural rigidity capable of absorbing the energy to the predetermined standard value in the bent condition below a predetermined stroke depending upon a distance in design between the bumper beams and the automobiles, etc.

For this reason, bumper beams have heretofore been inspected during production as to whether they meet the above-described two requirements or not, i.e., with respect to their striking energy-absorbing capability and flexural rigidity, in the following manner. Namely, a plurality of bumper beams are optionally taken out of the bumper beams produced as samples for inspection. Each of the bumper beams thus extracted is subjected to the so-called destructive test, as illustrated in FIG. 6, by fixedly supporting both ends of the bumper beam B on a pair of receiver jigs a in the same state as installed on an automobile (not shown) and then applying a flexural load by a pressing jig c having a pressing surface b of a predetermined radium of curvature such as a pole to the center of the bumper beam B until it is destroyed, thereby measuring the flexural load on and the bend stroke (hereinafter referred to as "bending strain") of the bumper beam B at the time it is destroyed.

More specifically, in the measurements of the flexural load on and the bending strain of the bumper beam B by the destructive test, as illustrated in FIG. 7 by way of example, the measured value as to the bending strain S of the bumper beam B linearly increases until just before the bumper beam B is destroyed as the flexural load F increases, and upon the destruction of the bumper beam B, it sharply increases in association with the deterioration in flexural rigidity of the bumper beam B, resulting in the destruction of the bumper beam B. In this case, supposing the absorption of energy in the bumper beam B is E, the following relationship is generally satisfied:

$$E = (\tfrac{1}{2}) \cdot F \cdot S \quad (1)$$

Therefore, the first requirement can be represented by the following relational expression:

$$Ed \geqq Ea \quad (2)$$

wherein Ea means a control value for determining whether the energy absorption in the destructive test is satisfactory or not, and Ed denotes an energy absorption at the moment the bumper beam B is destroyed. Here, the control value Ea as to the energy absorption corresponds to the predetermined standard value of the striking energy and is determined by various experiments according to the receiver jigs a and the pressing jig c.

Therefore, in order for the bumper beam B to meet the first requirement, a measuring point Pd of the flexural load Fd and bending strain Sd upon the destruction must lie in the upper side (on the drawing) of a hyperbola [hereinafter referred to as "hyperbola (3)"] represented by the following equation:

$$(\tfrac{1}{2}) \cdot F \cdot S = Ea \quad (3)$$

as indicated, for example, by a solid line in FIG. 7. On the basis of this required condition, the bumper beam B is inspected as to whether it meets the first requirement or not.

On the other hand, the second requirement means that supposing a control value as to the bending strain, which corresponds to the predetermined stroke in the destructive test and serves to determine whether it is satisfactory or not, is Sa, the energy absorption E is calculated in accordance with the equation (1) in a state where the bending strain S of the bumper beam B in the destructive test is not greater than the control value Sa of the bending strain and is not smaller than the control value Ea of the energy absorption. Here, the control value Sa of the bending strain is also determined by various experiments according to the receiver jigs a and the pressing jig c in the same manner as in the control value Ea of the energy absorption.

Therefore, in order for the bumper beam B to meet the second requirement, supposing the flexural load at the control value Sa as to the bending strain on the hyperbola (3) is Fa as shown in FIG. 7, a measured value Sx of the bending strain S at the flexural load Fa must be not greater than the control value Sa of the bending strain, for example, as indicated by a solid line in FIG. 7, i.e., $$Sx \geqq Sa \quad (4)$$

On the basis of this required condition, the bumper beam B is inspected as to whether it meets the second requirement or not. For example, a bumper beam B in which measured values as indicated by a broken line in FIG. 7 are obtained is judged to be poor in quality because the measured value of the bending strain S under the flexural load Fa exceeds the control value Sa of the bending strain.

As described above, the striking energy-absorbing capability and flexural rigidity of the bumper beam have heretofore been inspected by performing the destructive test, in which the flexural load is applied by the pressing jig c to the bumper beam fixedly supported on the receiver jigs a, to measure the flexural load Fd on and the bending strain Sd of the bumper beam upon destruction thereof as well as the bending strain Sx under the flexural load Fa, and then comparing the energy absorption Ed upon destruction, which is calculated from the flexural load Fd and the bending strain Sd, and the bending strain Sx with the predetermined control value Ea of the energy absorption and the predetermined control value Sa of the bending strain, respectively.

However, since the inspection of the bumper beams is conducted by the destructive test, the bumper beams tested cannot be used as products. Accordingly, many bumper beams are necessarily consumed at every inspection. Regarding the resinous bumper beams in particular, this has been an obstacle to the reduction in production costs of automobiles because they are expensive in general.

Moreover, since such a destructive test has been conducted for the bumper beams taken out as samples, there has been a potential problem that even when only one of the samples is judged to be poor in quality, many bumper beams produced before the test must be scrapped. In the resinous bumper beams in particular, the thermoplastic material requires a fixed period of time from its molding into a bumper beam to its complete crystallization. Therefore, the resinous bumper beams take a longer time before they come to be subjected to the destructive test as compared with the metallic bumper beams. Accordingly, bumper beams produced prior to the test are increased in number, leading to a possibility that a great number of bumper beams must be scrapped.

In order to solve such a disadvantage, it is desired to provide an inspection method capable of testing bumper beams produced and using bumper beams, which have been judged to be good in quality after the test, as products after the test.

In this case, since a bumper beam is generally designed and produced in such a manner that the energy absorption Ed at the moment it is destroyed exceeds sharply the control value Ea of the energy absorption as illustrated in FIG. 7, and at the time the bumper beam absorbs energy to the control value Ea, the bending strain S of the bumper beam falls within the range in which it linearly changes relative to the flexural load F and the bumper beam exhibits restoring property upon unloading it, it is considered, for example, that the above-described test is stopped at the time when the bumper beam absorbs energy to the control value Ea without continuing the test until the bumper beam is destroyed.

However, in the above inspection method, the bumper beam B is fixedly supported at both ends thereof on the receiver jigs a in the same state as installed on an automobile as illustrated in FIG. 6, and the flexural load is applied by pressing the pressing jig c having the pressing surface b of the predetermined radium of curvature against the center of the bumper beam B. Accordingly, the center and both ends of the bumper beam B are deformed due to pressing, so that it is difficult to use the bumper beam B after the inspection as a product.

Therefore, it is also considered that the receiver jigs and the pressing jig are exchanged so as not to impair the bumper beam upon applying the flexural load. However, the exchange of the receiver jigs and the pressing jig will make the condition of the flexural load to be applied to each portion of the bumper beam differed from that in the above destructive test in general. It is hence necessary to set up again the control values of the energy absorption and flexural strain according to new receiver jigs and pressing jig. In this case, it is desired that these control values can be set up with ease.

SUMMARY OF THE INVENTION

In view of the above-mentioned disadvantages of the prior art, it is an object of the present invention is to provide a method of inspecting bumper beams, which can solve the above-described disadvantages, to perform inspection with respect to the striking energy-absorbing capability and flexural rigidity of each of bumper beams produced. The inspected bumper beams, which have been judged to be good in quality after the inspection, are used products as is without any problems. Control values of the energy absorption and bending strain are easily set up, which serve to determine whether the bumper beams inspected are good in quality or not.

The present inventors have carried out various investigations. As a result, it has been found that when flexural load is applied to the center of a bumper beam by a pressing jig having a flat pressing surface and curved surfaces formed on both sides of the pressing surface in a state that the both ends of the bumper beam have been pivotably supported, the bumper beam can be gradually bent under the load without impairing the center and both ends thereof. In this case, it has also been found that the flexural load on and the bending strain of the bumper beam have substantially fixed correlations, respectively, with those in the above-described destructive test in which flexural load is applied to the center of a bumper beam fixedly supported at both ends, and new control values of the energy absorption and bending strain, which serve to determine whether the bumper beam inspected is good in quality or not, can be obtained by only correcting the control values of the energy absorption and bending strain in the destructive test.

Further, it has been found that with respect to the flexural rigidity of a resinous bumper beam molded, there is a substantially fixed correlation between the states before and after completion of crystallization of the resin material for the bumper beam.

According to one aspect of the present invention, there is thus provided a method of non-destructive inspection for resinous automotive bumper beams, in which a resinous automotive bumper beam molded is supported at both ends thereof and flexural load is applied to the center of the bumper beam, whereby the striking energy-absorbing capability and flexural rigidity of the bumper beam are inspected to determine whether the bumper beam is good in quality or not, said method comprising the steps of applying the flexural load to the center of the bumper beam by a pressing jig in a state where the both ends of the bumper beam have been pivotably supported to gradually bend the bumper beam; measuring or determining the bending strain and energy absorption of the bumper beam upon the application of the flexural load, said energy absorption being calculated from said bending strain and flexural load; and judging the bumper beam to be good in quality only when the energy absorption of the bumper beam reaches at least a control value of the energy absorption, which is set up in advance, in a state where the bending strain of the bumper beam is at most a control value of the bending strain, which is set up in advance, said control value of the energy absorption being determined by correcting the value of energy absorption upon destruction of a bumper beam, which has been found in a destructive test wherein the bumper beam is fixedly supported at both ends thereof and flexural load is applied to the center of the bumper beam until the bumper beam is destroyed, whereby the inspection of the bumper beam is conducted, said correction as to the energy absorption being performed on the basis of the correlation between a plurality of data as to the energy absorption and bending strain upon destruction of bumper beams in the destructive test and a plurality of data as to the energy absorption and bending strain when flexural load has been applied to individual bumper beams in the same manner as in the bending step to destroy the bumper beams, said control value of the bending strain being determined by correcting the bending strain in the destructive test, said correction as to the bending strain being performed on the basis of the correlation between a plurality of data as to the bending strain under predetermined flexural load under which the bumper beam is restorable in the destructive test and a plurality of data as to the bending strain when the predetermined flexural load has been applied to the individual bumper beams in the same manner as in the bending step, said application of the flexural load to the bumper beam being stopped at the time when the bumper beam is judged to be good in quality.

According to such an aspect of this invention, with respect to the resinous bumper beam judged to be good in quality in the judging step upon the inspection, the application of the flexural load by the pressing jig is stopped at the time when the energy absorption thereof reaches at least the control value of the energy absorption in the state that the bending strain of the bumper beam is at most the control value of the bending strain, and at the same time, the pressing surface of the pressing jig is flat and the bumper beam is pivotably supported at its both ends. Therefore, the bumper beam is restored to its original state without any deformation at its center and both ends after the inspection. Accordingly, all the bumper beams, which have been judged to be good in quality in the judging step, can be used as products as is.

According to this invention, the pressing jig has a flat pressing surface and curved surfaces formed jointly to the pressing surface and on both sides thereof and having a predetermined curvature.

Further, according to this invention, the inspection is also conducted before the crystallization of the bumper beam is completed, using control values of the energy absorption and bending strain, said control values having been set up in view of the reduction in flexural rigidity to that after completion of the crystallization. It is therefore possible to conduct the inspection of bumper beams in relatively short elapsed time after molding of the bumper beams.

The above and other objects, features and advantages of the present invention will become more apparent from the preferred embodiments of this invention, which will be described subsequently in detail with reference to the accompanying drawings.

DETAILED DESCRIPTION OF THE INVENTION AND PREFERRED EMBODIMENTS

A non-destructive inspection method for resinous bumper beams according to one embodiment of this invention will hereinafter be described with reference to FIGS. 1 through 5.

Figure 1:
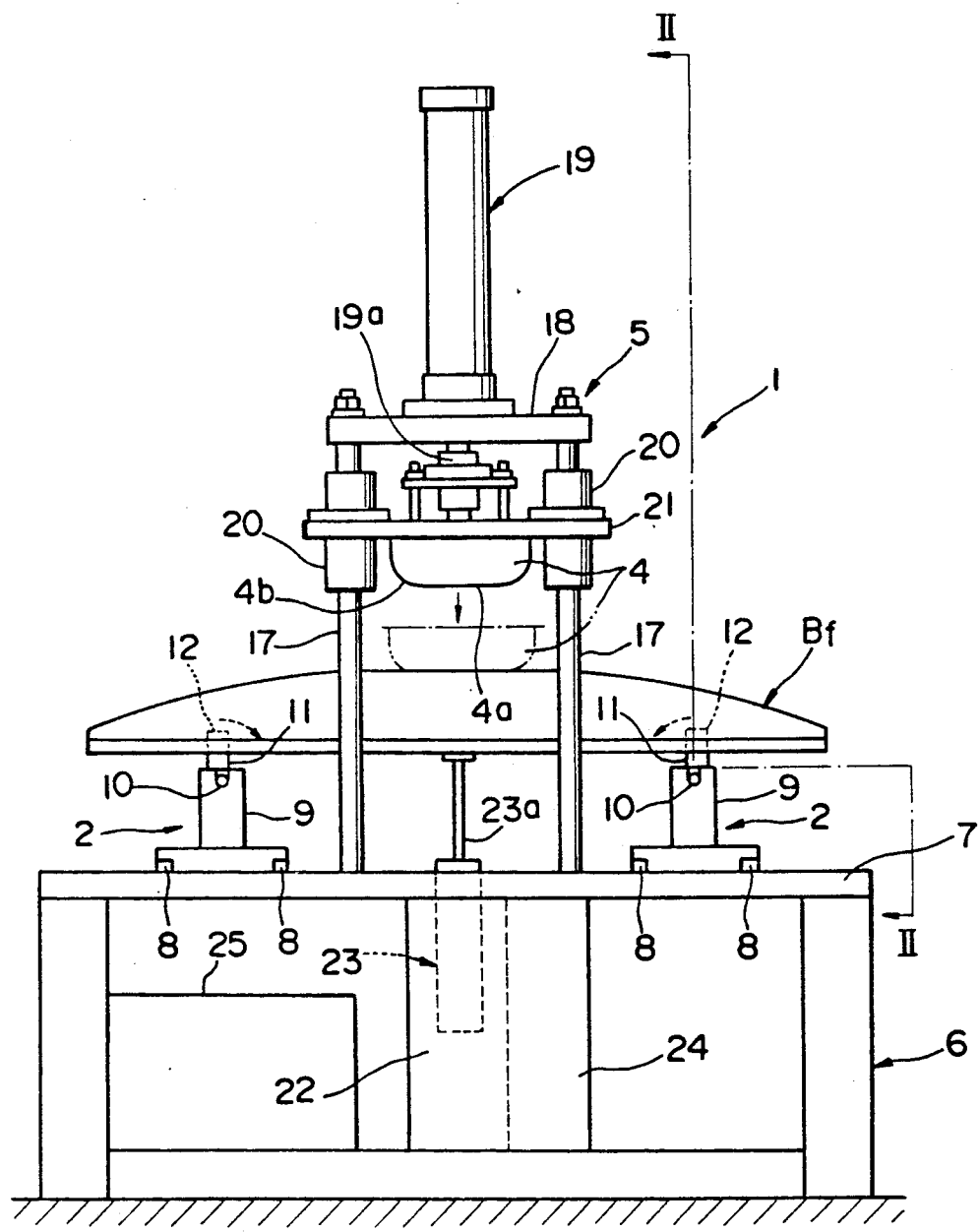
FIG. 1 is a front elevational view of an illustrative inspection apparatus making use of a non-destructive inspection method for resinous bumper beams according to this invention.
Figure 2:
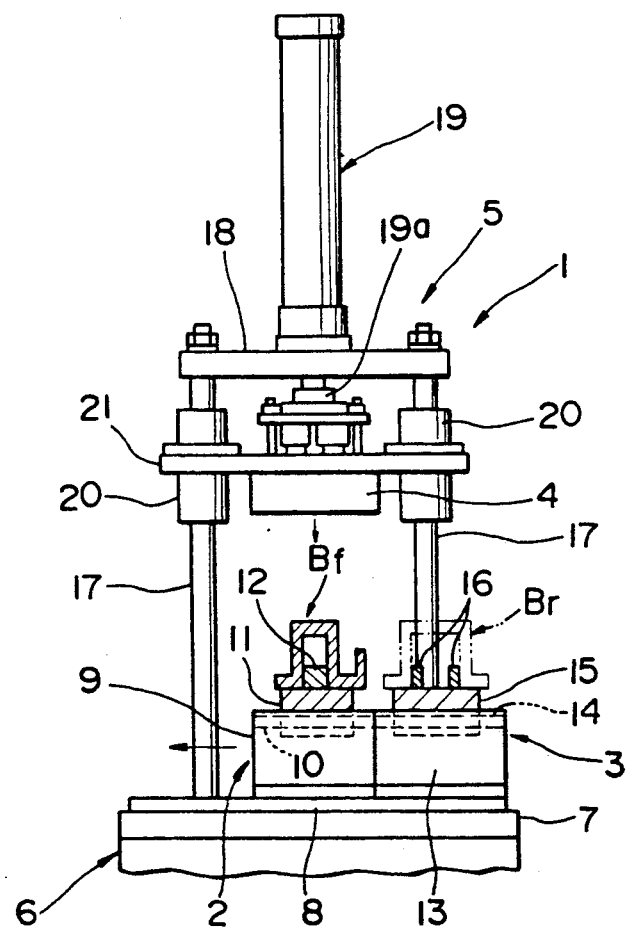
FIG. 2 is a cross-sectional view taken along line II—II of FIG. 1.

Referring now to FIGS. 1 and 2, reference characters Bf and Br indicate a front bumper beam and a rear bumper beam, respectively, both of which are made of a resin. Numeral 1 designates an inspection apparatus for testing both front and rear bumper beams Bf, Br.

As described above, both bumper beams Bf, Br are those produced by heating and softening a plurality of elongate stampable sheets (not illustrated) formed of a long-fiber-reinforced composite thermoplastic material containing longitudinally-stretching fibers as a reinforcement to laminate them and then press-molding the resulting laminate.

. In this embodiment, both bumper beams Bf, Br are such that the crystallization of the resin material has already been completed.

The inspection apparatus 1 is equipped with a pair of receiver jigs 2 for pivotably supporting both ends of a front bumper beam Bf, a pair of receiver jigs 3 for pivotably supporting both ends of a rear bumper beam Br, and a load-applying means 5 for applying flexural load to the center of each bumper beam Bf or Br through a pressing jig 4 in the form of a pendulum.

Each of the receiver jigs 2 comprises a movable mount 9 disposed movably on a pair of rails 8, which have been laid down longitudinally on both upper sides of a base 7 on a fixed frame 6, and a support 11 pivotably supported on the upper end of the movable mount 9 through a support shaft 10 extending longitudinally. The ends of the front bumper beam Bf are supported on the respective supports 11 as illustrated in FIG. 2, and respective fitting projections 12 provided on the supports 11 are fitted in the ends of the bumper beam Bf, so that the receiver jigs 2 can support the front bumper beam Bf pivotably on the support shafts 10.

Similarly, each of the receiver jigs 3 comprises a movable mount 13 disposed movably on the rails 8 and integrally with the movable mount 9 in the receiver jig 2, and a support 15 pivotably supported on the movable mount 13 through a support shaft 14. The ends of the rear bumper beam Br are supported on the respective supports 15 as illustrated in FIG. 2, and each pair of fitting projections 12 provided respectively on the supports 15 are fitted in the ends of the bumper beam Br, so that the receiver jigs 3 can support the rear bumper beam Br pivotably on the support shafts 14.

The receiver jigs 2 and 3 are separately moved on the rails 8 to both side positions of the pressing jig 4, which will be described subsequently, when they support respectively the bumper beams Bf and Br underneath the pressing jig 4.

The load-applying means 5 includes a fixed plate 18 fixedly disposed on upper ends of four guide rods 17 arranged between the receiver jigs 2 and extending uprightly from the base 7, a pressing cylinder 19 disposed fixedly and vertically on the fixed plate 18 and a lifting/lowering plate 21 vertically movably fitted on the guide rods 17 through tubes 20. The pressing jig 4 is fixedly attached to the lower surface of the lifting/lowering plate 21 and is vertically movable together with the lifting/lowering plate 21. The lifting/lowering plate 21 is fixed to the distal end of a piston rod 19a extending vertically telescopically from the pressing cylinder 19 to the lifting/lowering plate 21 through the fixed plate 18. The pressing jig 4 has a flat and wide pressing surface 4a formed on the lower side thereof and curved surfaces 4b formed respectively from one side of the pressing surface 4a to one side of the pressing jig 4 and having a fixed curvature as illustrated in FIG. 1.

In such a load-applying means 5, the piston rod 19a is caused to elongate by actuating the pressing cylinder 19 in the state that the bumper beam Bf or Br has been supported on the receiver jig 2 or 3 underneath the pressing jig 4 as described above to lower the pressing jig 4 together with the lifting/lowering plate 21 toward the bumper beam Bf or Br, whereby flexural load is applied downward to the center of the bumper beam Bf or Br through the pressing surface 4a of the pressing jig 4.

Incidentally, in FIG. 1, a bending strain meter 22 is provided for measuring the bending strain of the bumper beam Bf or Br applied with the flexural load by the load-applying means 5. According to the bending strain meter 22, the bending strain is measured by bringing the distal end surface of a piston rod 23a, which extends vertically telescopically from a cylinder 23 disposed downward on the lower side of the base 7 to a bumper beam Bf or Br to be applied with the flexural load through the base 7, into contact with the lower surface of the bumper beam Bf or Br to detect the lowering level of the piston rod 23a upon the application of the flexural load.

Also, in FIG. 1, a load meter 24 for measuring the flexural load and a control unit 25 are provided for controlling the actuation of the pressing cylinder 19 according to the flexural load and bending strain to be measured, etc.

The inspection of bumper beams Bf, Br, for example, a front bumper beam Bf, by such an inspection apparatus 1 is conducted as follows.

Namely, the front bumper beam Bf is first of all supported on the receiver jigs 2 underneath the pressing jig 4 of the load-applying means 5 as described above. In this state, the pressing cylinder 19 is actuated to lower the pressing jig 4 toward the bumper beam Bf. The pressing jig 4 is further lowered to apply flexural load to the center of the bumper beam Bf through the pressing surface 4a of the pressing jig 4, whereby the bumper beam Bf is gradually bent while the flexural load is progressively increased.

At this time, the supports 11 of the receiver jigs 2 are pivoted on the respective support shafts 10 following the bending of the bumper beam Bf. In addition, since the pressing surface 4a of the pressing jig 4 is flat and the curved surfaces 4b are formed on the sides of the pressing surface 4a, the bumper beam Bf is bent without deformation of the center and both ends thereof.

On the other hand, at the same time, the bending strain of and the flexural load on the bumper beam Bf are successively measured by the bending strain meter 22 and the load meter 24, respectively. From these measurements, the energy absorption of the bumper beam Bf is successively calculated in accordance with the equation (1).

In basically the same manner as in the destructive test, the quality of the bumper beam Bf is judged by whether it meets the first and second requirements or not. Namely, the energy absorption and bending strain of the bumper beam Bf are compared with the control values of the energy absorption and bending strain, which are set up in advance as described below. The bumper beam Bf is judged to be good in quality when the energy absorption of the bumper beam Bf reaches at least the control value of the energy absorption in a state where the bending strain of the bumper beam Bf is at most the control value of the bending strain. On the contrary, the bumper beam Bf is judged to be poor in quality when the bending strain of the bumper beam Bf reaches the control value of the bending strain in a state where the energy absorption of the bumper beam Bf is less than the control value of the energy absorption. In this inspection, the application of the flexural load to the bumper beam Bf by the pressing cylinder 19 is stopped at the time when the quality of the bumper beam Bf has been judged. The pressing jig 4 is then lifted up in the reverse fashion to separate it from the bumper beam Bf.

With respect to the inspection of a rear bumper beam Br on the other hand, after the front bumper beam Bf is taken out of the receiver jigs 2 in FIG. 2, the receiver jigs 2, 3 are moved on the rails 8 to position the receiver jigs 3 at the side positions of the pressing jig 4. As described above, the rear bumper beam Br is then supported on the receiver jigs 3 underneath the pressing jig 4 of the load-applying means 5. In this state, the inspection is conducted in exactly the same manner as in the front bumper beam Bf.

Manners in which control values as to the energy absorption and bending strain in such an inspection are set up will hereinafter be described in detail with reference to the flow charts illustrated in FIGS. 3 and 4.

First, the control value of the energy absorption will be described. Since this control value is the quantity of energy which a bumper beam must absorb before its destruction when flexural load is applied thereto as expressed by the relational expression (2), the control value of the energy absorption for the front bumper beam Bf by way of example is set up based on the measured data as to the energy absorption a the time when the bumper beam is destroyed.

Figure 6:
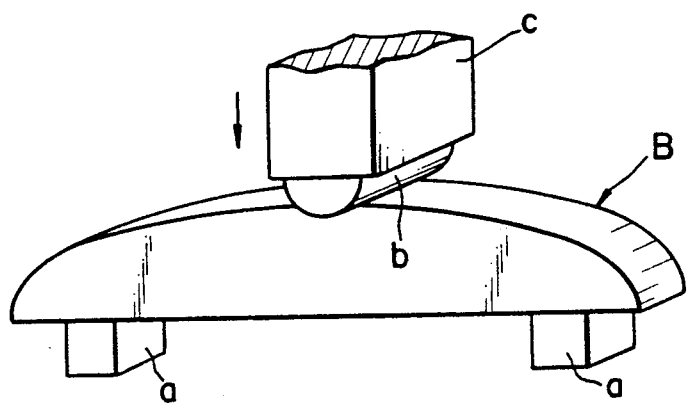
FIGS. 6 and 7 are explanatory views illustrating a conventional inspection method for the bumper beams.

Therefore, in this embodiment, the control value of the energy absorption for the front bumper beam Bf by way of example was set up in the following manner. As illustrated in FIG. 3, a plurality of front bumper beams Bf were first subjected to a destructive test making use of the inspection apparatus 1 in this embodiment in accordance with the same method as in the conventional inspection (hereinafter referred to as "trial destructive test") and at the same time, to the conventional destructive test (hereinafter referred to as "standard destructive test") making use of the receiver jigs a and the pressing jig c (see FIG. 6), whereby the bending strain Sd of and the flexural load Fd on each bumper beam Bf upon its destruction were measured in both destructive tests.

Then, the bending strain Sd and flexural load Fd upon the destruction in the trial destructive test were correlated respectively with the bending strain Sd and flexural load Fd upon the destruction in the standard destructive test, thereby determining correction factors Cs, Cf for correcting the bending strain Sd and flexural load Fd upon the destruction in the standard destructive test to the bending strain Sd and flexural load Fd upon the destruction in the trial destructive test, respectively.

More specifically, respective average values Sma, Smb of the measured data of the bending strain Sd in the standard and trial destructive tests were first found and the correction factor Cs of the bending strain Sd was then determined from both average values Sma, Smb in accordance with the following equation:

$$Cs = Smb/Sma \qquad (5)$$

Similarly, the correction factor Cf of the flexural load Fd was determined from respective average values Fma, Fmb of the measured data of the flexural load Sd in the standard and trial destructive tests in accordance with the following equation:

$$Cf = Fmb/Fma \qquad (6)$$

The bending strain Sd and flexural load Fd upon the destruction in the trial destructive test are found by multiplying the bending strain Sd and flexural load Fd upon the destruction in the standard destructive test by the correction factors Cs, Cf, respectively. Since the energy absorption E of the bumper beam Bf, Br is proportional to the product of the flexural load F and the bending strain S as apparent from the equation (1), the control value Eb as to the energy absorption in the inspection apparatus 1 was set up from the control value Ea of the energy absorption for the receiver jigs a and the pressing jig c in accordance with the following equation:

$$Eb = Cs \cdot Cf \cdot Ea \qquad (7)$$

On the other hand, the control value as to the bending strain S in the inspection apparatus 1 is basically a control value within the range in which the bending strain of a bumper beam linearly changes relative to the flexural load. Accordingly, the control value of the bending strain for a front bumper beam Bf by way of example is set up based on the data as to the bending strain within the range in which the bending strain linearly changes relative to the flexural load.

Figure 7:
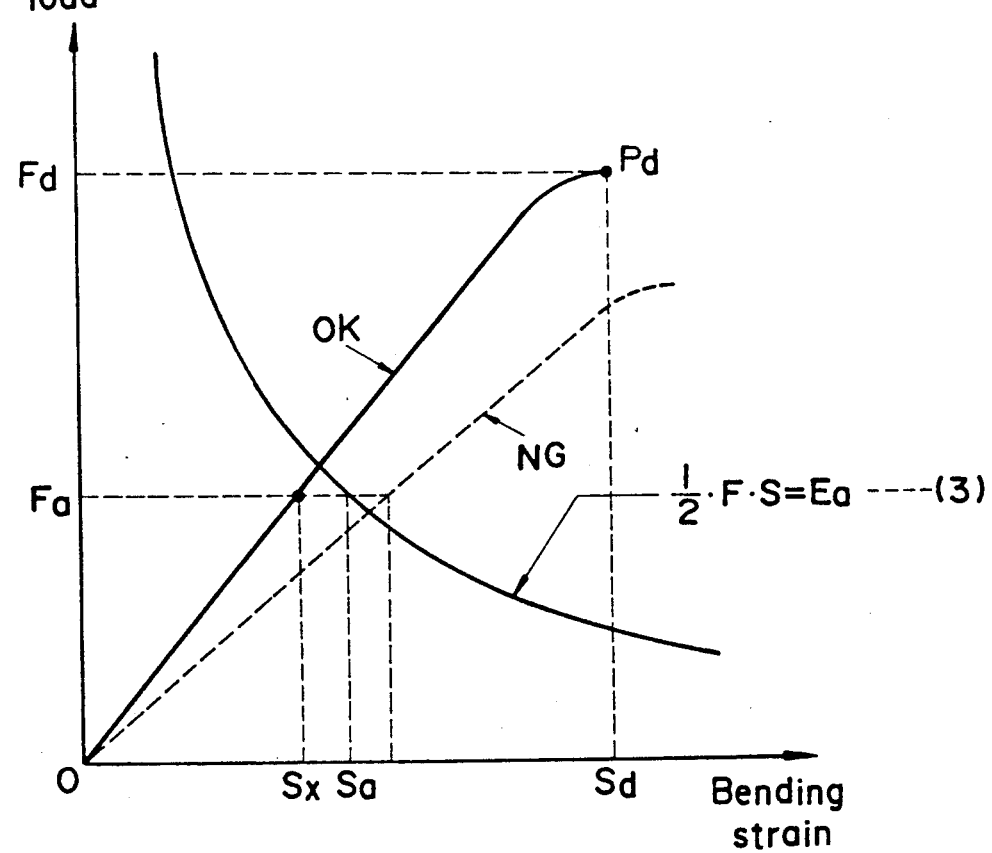

Namely, in this embodiment, the control value of the bending strain for the front bumper beam Bf by way of example was set up in the following manner. As illustrated in FIG. 4, a plurality of front bumper beams Bf were first subjected to the trial destructive test and the standard destructive test, whereby the bending strains Sx under, for example, fixed flexural load Fa (see FIG. 7) under which the bending strain linearly changed were separately measured.

In the same manner as described above, a correction factor Css for correcting the bending strain Sx under the flexural load Fa in the standard destructive test to the bending strain Sx under the flexural load Fa in the trial destructive test was then determined from respective average values Smy, Smx of the measured data of the bending strain Sx under the flexural load Fa in the trial and standard destructive tests in accordance with the following equation:

$$Css = Smy/Smx \qquad (8)$$

The bending strain Sx under the flexural load Fa in the trial destructive test is found by multiplying the bending strain Sx under the flexural load Fa in the standard destructive test by the correction factor Css. Accordingly, the control value Sb as to the bending strain under the flexural load Fa in the inspection apparatus 1 was set up from the control value Sa of the bending strain for the receiver jigs a and the pressing jig c in accordance with the following equation:

$$Sb = Css \cdot Sa \qquad (9)$$

Figure 3:
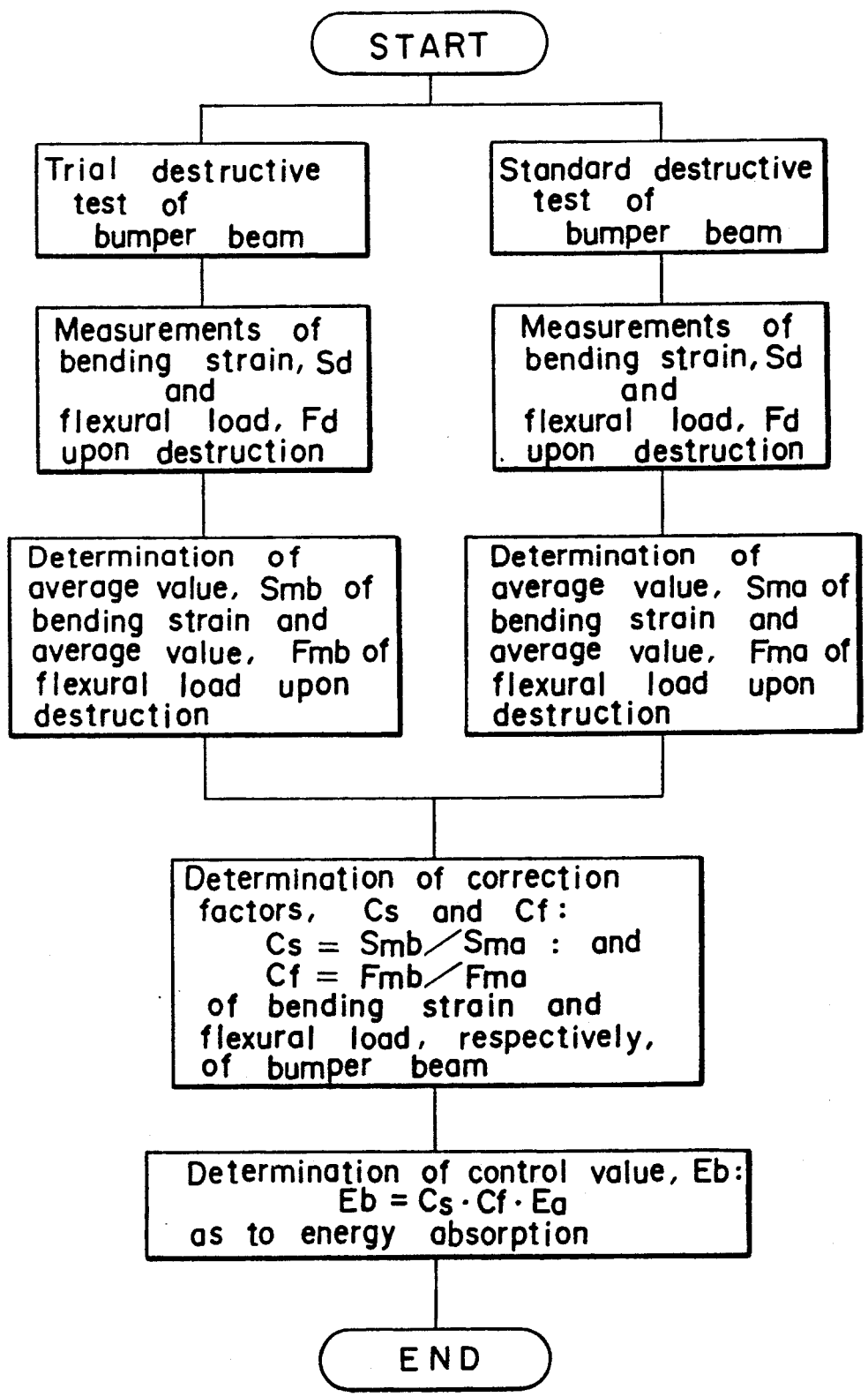
FIGS. 3 and 4 are flow charts illustrating how to set up control values which serve to determine whether the bumper beams are good in quality or not.
Figure 4:
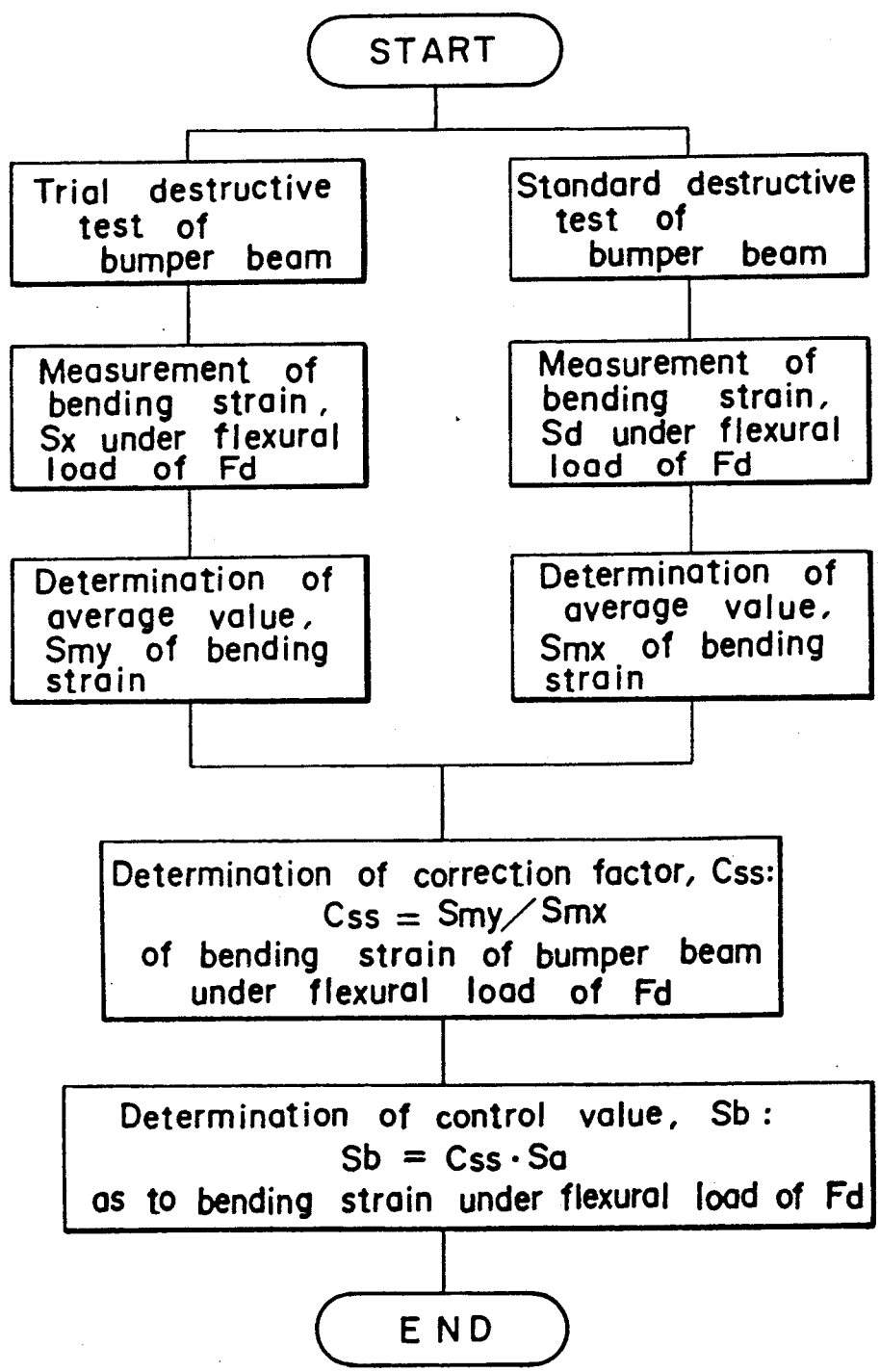

In addition, new control values as to the energy absorption and bending strain for the rear bumper beam Br were also determined in accordance with the flow charts in FIGS. 3 and 4, respectively, in exactly the same way as described above.

A manner in which the quality, for example, of the front bumper beam Bf is judged from these control values Eb, Sb when the inspection of the bumper beam Bf is conducted in the above-described manner will hereinafter be described in detail with reference to FIG. 5.

Figure 5:
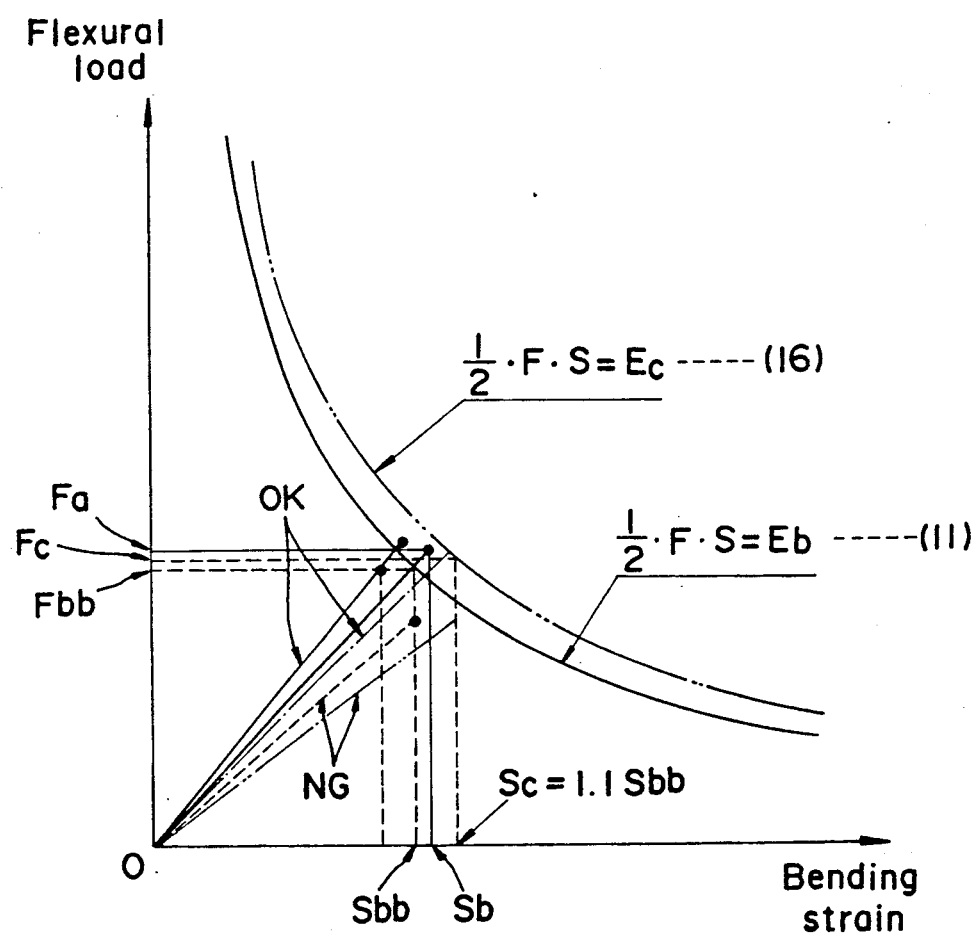
FIG. 5 is a diagram illustrating the inspection method for the bumper beams.

First, the above-mentioned first requirement, in the inspection apparatus 1, can be represented by the following relational expression corresponding to the relational expression (2):

$$Ed \geq Eb \qquad (10)$$

wherein Ed means an energy absorption at the moment the bumper beam Bf is destroyed. In this case, the bending strain S of the bumper beam Bf during the inspection is increased as the flexural load F increases, as described above (see FIG. 7). Therefore, it is only necessary that the energy absorption E calculated from the bending strain S and the flexural load F in accordance with the equation (1) in the course of the inspection is at least the control value Eb of the energy absorption. For this reason, in order for the bumper beam Bf to meet the first requirement, the measuring point of the bending strain S and flexural load F by the inspection apparatus 1 may reach, during increase of the flexural load F, the upper side (on the drawing) of a hyperbola [hereinafter referred to as "hyperbola (11)"] represented by the following equation corresponding to the equation (3):

$$(\tfrac{1}{2}) \cdot F \cdot S = Eb \qquad (11)$$

as indicated, for example, by a solid line in FIG. 5.

On the other hand, the above-mentioned second requirement, in the inspection apparatus 1, can be represented by the following relational expression corresponding to the relational expression (4):

$$Sy \leq Sb \qquad (12)$$

wherein Sy means a measured value of the bending strain S under the fixed flexural load Fa. In this case, the control value Sb of the bending strain is a control value of the bending strain S at the time when the energy absorption E of the bumper beam Bf reaches the control value Eb of the energy absorption in view of its object. However, as apparent from the above, since the correction for the control value Eb of the energy absorption is a correction within the range in which the bending strain S of the bumper beam Bf, Br does not linearly change relative to the flexural load F, while the correction for the control value Sb of the bending strain is a correction within the range in which the bending strain S linearly changes relative to the flexural load F, a point (Sb, Fa) in the control value Sb of the bending strain, which has been found from the above-described correction does not lie on the hyperbola (11), for example, as illustrated in FIG. 5.

Therefore, in this embodiment, a control value as to the bending strain in the inspection apparatus 1 was defined as follows. Namely, supposing an intersection of a straight line connecting the origin 0 and the point (Sb, Fa), and the hyperbola (11) is a point (Sbb, Fbb) as shown in FIG. 5, the relational expression (4) is identical to the fact that a measured value Syy of the bending strain S under the flexural load Fbb satisfies the following relational expression:

$$Syy \leq Sbb \qquad (13)$$

Therefore, the Sbb is taken as a control value of the bending strain in the inspection apparatus 1. Namely, in order for the bumper beam Bf to meet the second requirement in the inspection apparatus 1, it is only necessary to satisfy the relational expression (13) under the flexural load Fbb, for example, as indicated by a solid line in FIG. 5.

Accordingly, by the above-described inspection making use of the inspection apparatus 1, a bumper beam Bf whose measured value as to the bending strain S is at most the control value Sbb of the bending strain and whose energy absorption E calculated from the bending strain S and flexural load F is at least the control value Eb of the energy absorption, for example, as indicated by the solid line in FIG. 5, is judged to be good in quality because it meets both first and second requirements. On the other hand, a bumper beam Bf whose bending strain S reaches the control value Sbb of the bending strain before its energy absorption E reaches the control value Eb of the energy absorption, for example, as indicated by a broken line in FIG. 5, is judged to be poor in quality because it does not satisfy the relational expression (13).

In this case, since the application of the flexural load F to the bumper beam Bf, which has been judged to be good in quality, is stopped at the time when the energy absorption E has reached at least the control value Eb of the energy absorption as described above, the bumper beam Bf is restored to its original state.

According to the inspection apparatus 1, as described above, since the bumper beam Bf judged to be good in quality is restores to its original state without impairing it, this bumper beam can be used as a product without a hindrance. In addition, since the control value Eb of the energy absorption and the control value Sbb of the bending strain for the inspection apparatus 1 are found by correcting the control value Ea of the energy absorption and the control value Sa of the bending strain in the standard destructive test, respectively, these control values can be set up with relative ease.

Incidentally, the judgment of quality for the rear bumper beam Br is also conducted using the control values of the energy absorption and the bending strain for the bumper beam Br in the same manner as in the front bumper beam Bf. A rear bumper beam Br judged to be good in quality can be used as a product without a hindrance.

A manner in which bumper beams Bf, Br are test by the inspection apparatus 1 before the resin material of the bumper beams Bf, Br is completely crystallized will be described with reference to FIG. 5.

In this case, the flexural rigidity of the bumper beams Bf, Br is decreased as compared with those the resin material of which has been crystallized. Therefore, such bumper beams Bf, Br become easy to bend in proportion to the reduction of the flexural rigidity when the flexural load F is applied thereto by the inspection apparatus 1. For example, supposing the reduction of the flexural rigidity in a front bumper beam Bf is 10%, the bending strain S of the bumper beam Bf is increased by 10%.

Therefore, a control value Ec as to the energy absorption and a control value Sc as to the bending strain in this case (before completion of the crystallization) can be found from the control values Eb and Sbb of the energy absorption and bending strain in the above-described case (after completion of the crystallization) in accordance with the following equations, respectively:

$$Ec = 1.1 \cdot Eb \qquad (14)$$

$$Sc = 1.1 \cdot Sbb \qquad (15)$$

Accordingly, the first requirement in this case means that the measuring point of the bending strain S and flexural load F by the inspection apparatus 1 reaches, during increase of the flexural load F, the upper side of a hyperbola [hereinafter referred to as "hyperbola (16)"] represented by the following equation corresponding to the equation (11):

$$(\tfrac{1}{2}) \cdot F \cdot S = Ec \qquad (16)$$

and indicated by a two-dot chain line in FIG. 5, while the second requirement means that supposing the flexural load at the control value Sc of the bending strain in the hyperbola (16) is Fc, a measured value Sz of the bending strain S under the flexural load Fc satisfies the following relational expression corresponding to the relational expression (13):

$$Sz \leq Sc \qquad (17)$$

Specifically, for example, a bumper beam Bf in which measured values of the bending strain S and flexural load F as indicated by a dashed line in FIG. 5 are obtained is judged to be good in quality, while a bumper beam Bf in which measured values of the bending strain S and flexural load F as indicated by a two-dot chain line in FIG. 5 are obtained is judged to be poor in quality.

As described above, when the control value Ec of the energy absorption and the control values Sc of the bending strain are set up in view of the reduction in flexural rigidity of the front bumper beams Bf before completion of the crystallization, it is possible to conduct their inspection in relatively short elapsed time after the molding of the bumper beams Bf. This is also to be exactly repeated in the rear bumper beams Br.

Although the present invention has been described above with reference to the preferred embodiments thereof, it should be understood that the invention is not limited thereto and that various modifications and changes in form and details can be made therein without departing from the spirit and scope of the invention.

What is claimed is:

1. A method of non-destructive inspection for resinous automotive bumper beams, in which a molded resinous automotive bumper beam is supported at both ends thereof and a flexural load is applied to approximately the center of the bumper beam, whereby the striking energy-absorbing capability and flexural rigidity of the bumper beam are inspected for determining the quality of the bumper beam, said method comprising the following steps:

applying the flexural load to approximately the center of the bumper beam by a pressing jig wherein both ends of the bumper beam are pivotably supported for gradually bending the bumper beam;

measuring the bending strain of the bumper beam upon the application of the flexural load, said energy absorption being calculated from said bending strain and flexural load;

judging the quality of the bumper beam only when the energy absorption of the bumper beam reaches at least a predetermined control value of the energy absorption in a state wherein the bending strain of the bumper beam is at most at a predetermined control value of the bending strain;

determining the control value of the energy absorption by correcting the value of energy absorption upon destruction of a bumper beam subjected to a destructive test wherein the bumper beam is fixedly supported at both ends thereof and the flexural load is applied to the center of the bumper beam until the bumper beam is destroyed, wherein the correcting of the energy absorption is performed on the basis of the correlation between a plurality of data as to the energy absorption and bending strain upon destruction of bumper beams in the destructive test and a plurality of data as to the energy absorption and bending strain when flexural load is applied to individual bumper beams in the same manner as in the bending step to destroy the bumper beams;

determining the control value of the bending strain by correcting the bending strain in the destructive test, wherein the correcting of the bending strain is performed on the basis of the correlation between a plurality of data as to the bending strain under predetermined flexural load under which the bumper beam is restorable in the destructive test and a plurality of data as to the bending strain when the predetermined flexural load has been applied to the individual bumper beams in the same manner as in the bending step; and stopping the application of the flexural load to the bumper beam at the time when the bumper beam is judged to be of good quality.

2. The method of claim 1, wherein the step of applying the flexural load includes utilizing the pressing jig and providing a flat pressing surface and surfaces having predetermined curvatures formed jointly to the pressing surface and on both sides thereof.

3. The method of claim 1, wherein the bumper beam to which the flexural load is applied in the bending step is in a state wherein a crystallization after molding is not completed, and the control value of the energy absorption and the control value of the bending strain are predetermined in view of the reduction in flexural rigidity which occurs after completion of the crystallization.

* * * * *